United States Patent
Lee et al.

(10) Patent No.: US 7,574,252 B2
(45) Date of Patent: Aug. 11, 2009

(54) APPARATUS AND METHOD FOR MEASURING FAT

(75) Inventors: Jong-youn Lee, Yongin-si (KR); Bo Li, Hangzhou (CN); Kye-jin Jeon, Suwon-si (KR); Kyung-ho Kim, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 166 days.

(21) Appl. No.: 11/192,117

(22) Filed: Jul. 29, 2005

(65) Prior Publication Data

US 2006/0079789 A1 Apr. 13, 2006

(30) Foreign Application Priority Data

Oct. 11, 2004 (KR) .......... 10-2004-0081058

(51) Int. Cl.
*A61B 6/00* (2006.01)
(52) U.S. Cl. .................... 600/473
(58) Field of Classification Search ........ 600/476, 600/407, 323, 442, 449, 316, 473; 250/340, 250/358; 324/439; 128/664
See application file for complete search history.

(56) References Cited

U.S. PATENT DOCUMENTS

| 4,447,725 | A | * | 5/1984 | Biggs et al. ............ 250/339.12 |
| 4,633,087 | A | | 12/1986 | Rosenthal et al. |
| 4,850,365 | A | | 7/1989 | Rosenthal |
| 5,941,825 | A | * | 8/1999 | Lang et al. ............ 600/449 |
| 5,989,283 | A | * | 11/1999 | Wilkens ............ 607/88 |
| 6,441,977 | B1 | * | 8/2002 | Mashima ............ 359/831 |
| 6,584,340 | B1 | * | 6/2003 | Horiuchi et al. ............ 600/473 |
| 6,587,702 | B1 | * | 7/2003 | Ruchti et al. ............ 600/310 |
| 2005/0197583 | A1 | * | 9/2005 | Chance ............ 600/476 |

FOREIGN PATENT DOCUMENTS

WO   WO 01/52725    7/2001
WO   WO 2004/080276  9/2004

OTHER PUBLICATIONS

European Search Report for Application No. 05252131.7-2305 dated Dec. 21, 2005 (5 pages).

* cited by examiner

*Primary Examiner*—Eric F Winakur
*Assistant Examiner*—Lawrence N Laryea
(74) *Attorney, Agent, or Firm*—Staas & Halsey LLP

(57) ABSTRACT

A method and apparatus for measuring fat thickness in a target body part are provided. The apparatus includes a light emitter emitting near infrared rays, an inner reflector having a reflecting plane outside to reflect the near infrared rays emitted by the light emitter, an outer reflector surrounding the inner reflector and having a reflecting plane inside to reflect the near infrared rays emitted by the light emitter, a light receiver receiving light reflected from the target body part in response to the near infrared rays, and a calculator calculating the fat thickness in the target body part using the light received by the light receiver.

17 Claims, 6 Drawing Sheets

APPARATUS AND METHOD FOR MEASURING FAT

CROSS REFERENCE TO RELATED APPLICATION

This application claims the priority of Korean Patent Application No. 10-2004-81058, filed on Oct. 11, 2004, in the Korean Intellectual Property Office, the disclosure of which is incorporated herein in its entirety by reference.

BACKGROUND OF THE INVENTION

1. Field of the Invention

The present invention relates to an apparatus and method for measuring fat thickness, and more particularly, to an apparatus and method for measuring fat thickness in a part of a human body by radiating light at the body part.

2. Description of the Related Art

The human body is mainly comprised of four components: water, protein, fat, and minerals. The ratio of these components in the body is different depending on sex, age, and race, but it is roughly 55:20:20:5. The ratio of the four components can be obtained from the amount of water in the body since protein and water are major components of human muscle and are proportional to each other. For example, if healthy muscle is comprised of about 73% water, the other 27% is protein. Minerals form bones, a weight of which is closely related with the muscle weight. In detail, the amount of protein and the amount of minerals can be obtained using the amount of water in the body, and the amount of fat in the body is obtained by subtracting the sum of the amounts of water, protein, and minerals from the body weight. Conventionally, bioelectrical impedance analysis (BIA) is most widely used to measure body fat. Besides, hydrodensitometry is also used.

In the BIA, a body fat rate is measured based on the fact that the amount of hydrodensitometry water in the body is inversely proportional to the electrical resistance of the body. The BIA is advantageous in that measurement is simple, quick, and non-invasive. When a weak alternating current (AC) electrical signal is applied to the human body, electricity flows along water having high conductivity in the body. According to the amount of water, the size of a passage through which the electricity flows is determined. A value measured in this situation indicates the bio-impedance. In calculating the amount of a body component using the bio-impedance, an AC of about 1 mA in a frequency band of 50 kHz is applied to the human body. When the AC flows in the body, body resistance is measured and the amount of water in the body is obtained using the body resistance. The amount of protein and the amount of minerals are obtained using the amount of water. A body fat rate is obtained using the amounts of protein and minerals and the weight of the body.

FIG. 1 is a perspective view of a conventional apparatus for measuring a body fat rate using near infrared rays. The apparatus radiates near infrared rays at a human body and measures a body fat rate. To accurately measure the body fat rate, near infrared rays must be uniformly radiated at a target body part and a constant amount of near infrared rays must be radiated at every measurement. The apparatus shown in FIG. 1 radiates near infrared rays at a target body part using four light emitters 100, 110, 120, and 130. To increase uniformity of radiation of near infrared rays, it is necessary to increase the number of light emitters or the length of the apparatus.

FIG. 2 illustrates a perspective view of another conventional apparatus for measuring a body fat rate using near infrared rays, to explain a method of setting a measurement position of the apparatus. For continuity of near infrared rays at every measurement, two marks 210 and 220 of the apparatus 200 must be always aligned when measurement is performed.

As described above, in the conventional apparatuses and methods for measured fat, it is necessary to increase the number of light emitters or the length of a measuring apparatus to satisfactorily uniformize the amount of near infrared rays radiated at a target body part. As a result, manufacturing cost increases and miniaturization cannot be accomplished. In addition, the conventional technology is inconvenient because a measurement position must be set at every measurement. Moreover, a fat rate in a whole human body can be measured, but the amount of fat in a part of the body cannot be measured.

SUMMARY OF THE INVENTION

Additional aspects and/or advantages of the invention will be set forth in part in the description which follows and, in part, will be apparent from the description, or may be learned by practice of the invention.

The present invention provides a method and apparatus for measuring fat thickness in a target body part using near infrared rays emitted by a single light emitter.

According to an aspect of the present invention, there is provided an apparatus for measuring fat thickness in a target body part of a person, including a light emitter emitting near infrared rays, an inner reflector having a reflecting plane outside to reflect the near infrared rays emitted by the light emitter, an outer reflector surrounding the inner reflector and having a reflecting plane inside to reflect the near infrared rays emitted by the light emitter, a light receiver receiving light reflected from the target body part in response to the near infrared rays, and a calculator calculating the fat thickness in the target body part using the light received by the light receiver.

The apparatus may further include a conductive window transmitting the near infrared rays emitted by the light emitter to the target body part.

The near infrared rays may have a wavelength of 930 nm or 1040 nm, and the reflecting planes may be formed using aluminum.

The light receiver may be a pin type silicon detector. The calculator may include a ratio calculator calculating a ratio of intensity of the light received by the light receiver to intensity of the near infrared rays radiated at the target body part to obtain absorptance, and a thickness calculator calculating the fat thickness in the target body part using the calculated absorptance and a relationship between the absorptance and the fat thickness.

The relationship between the absorptance and the fat thickness may be determined by a relationship between a ratio of intensity of light reflected from a fat to intensity of near infrared rays radiated at the fat and a thickness of the fat measured using an ultrasonic wave.

The calculator may include a ratio calculator calculating a ratio of intensity of the light received by the light receiver to intensity of the near infrared rays radiated at the target body part to obtain absorptance, and a thickness calculator calculating the fat thickness in the target body part using two absorptances calculated with respect to the near infrared rays having two different wavelengths and a relationship between the absorptances and the fat thickness.

According to another aspect of the present invention, there is provided a method of measuring fat thickness in a target body part of a person, including radiating near infrared rays at a fat sample, measuring an absorptance of the fat sample with respect to the near infrared rays, measuring a thickness of the fat sample using an ultrasonic wave, generating an equation defining a relationship between the absorptance and the fat thickness, generating and radiating near infrared rays at the target body part, receiving light reflected from the target body part in response to the near infrared rays, calculating a ratio of intensity of the light reflected from the target body part to intensity of the near infrared rays radiated at the target body part to obtain absorptance of the target body part, and calculating the fat thickness in the target body part using the calculated absorptance and the generated equation.

The near infrared rays may be emitted by a single light emitter and may have a wavelength of 930 nm or 1040 nm.

According to still another aspect of the present invention, there is provided a method of measuring fat thickness in a target body part of a person, including radiating near infrared rays having a first wavelength at a fat sample and measuring an absorptance of the fat sample with respect to the near infrared rays having the first wavelength; radiating near infrared rays having a second wavelength at the fat sample and measuring an absorptance of the fat sample with respect to the near infrared rays having the second wavelength; measuring a thickness of the fat using an ultrasonic wave; generating an equation defining a relationship between the absorptances respectively obtained at the first and second wavelengths and the fat thickness; radiating near infrared rays having the first wavelength at the target body part, receiving light reflected from the target body part, and calculating a ratio of intensity of the light reflected from the body part to intensity of the near infrared rays radiated at the target body part to obtain absorptance of the target body part; radiating near infrared rays having the second wavelength at the target body part, receiving light reflected from the target body part, and calculating a ratio of intensity of the light reflected from the body part to intensity of the near infrared rays radiated at the target body part to obtain absorptance of the target body part; and calculating the fat thickness in the target body part using the two calculated absorptances and the generated equation.

The first and second wavelengths may be 930 nm and 1040 nm, respectively. The near infrared rays may be emitted by a single light emitter.

The method of measuring fat thickness may be implemented as a computer program recorded in a computer readable recording medium.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE PREFERRED EMBODIMENTS

Figure 1:
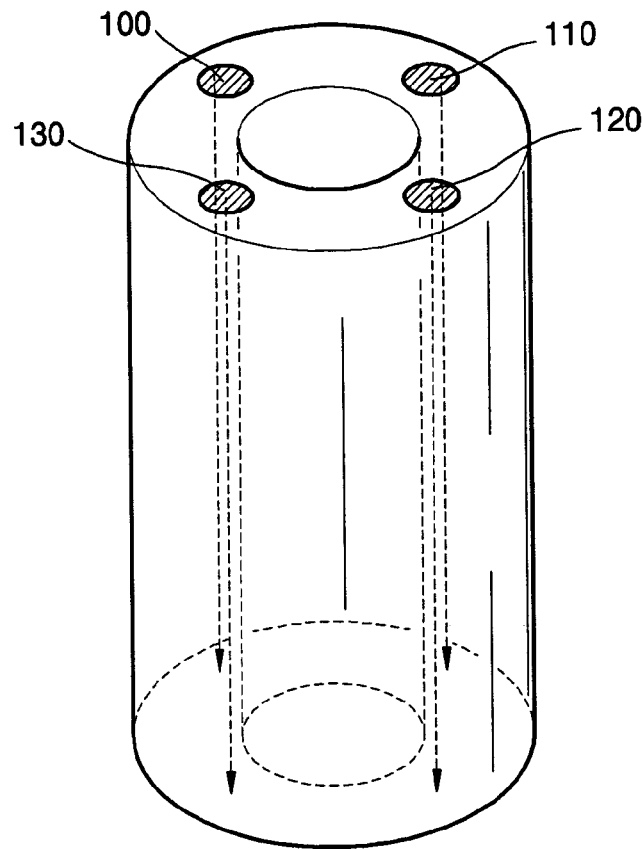
FIG. 1 is a perspective view of a conventional apparatus for measuring a body fat rate using near infrared rays.
Figure 2:
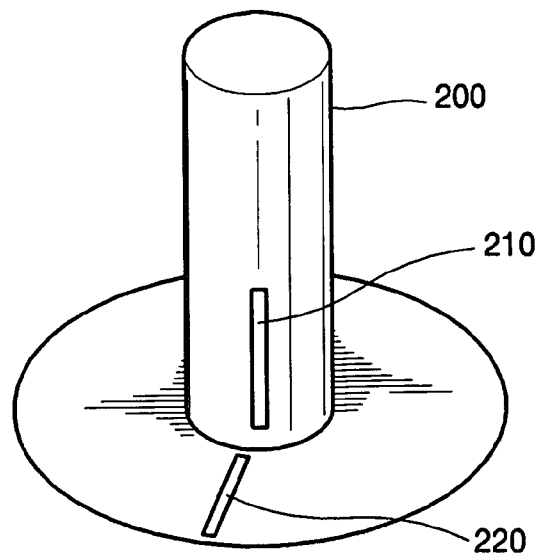
FIG. 2 is a perspective view of another conventional apparatus for measuring a body fat rate using near infrared rays to explain a method of setting a measurement position of the apparatus.

Reference will now be made in detail to the embodiments of the present invention, examples of which are illustrated in the accompanying drawings, wherein like reference numerals refer to the like elements throughout. The embodiments are described below to explain the present invention by referring to the figures.

Figure 3:
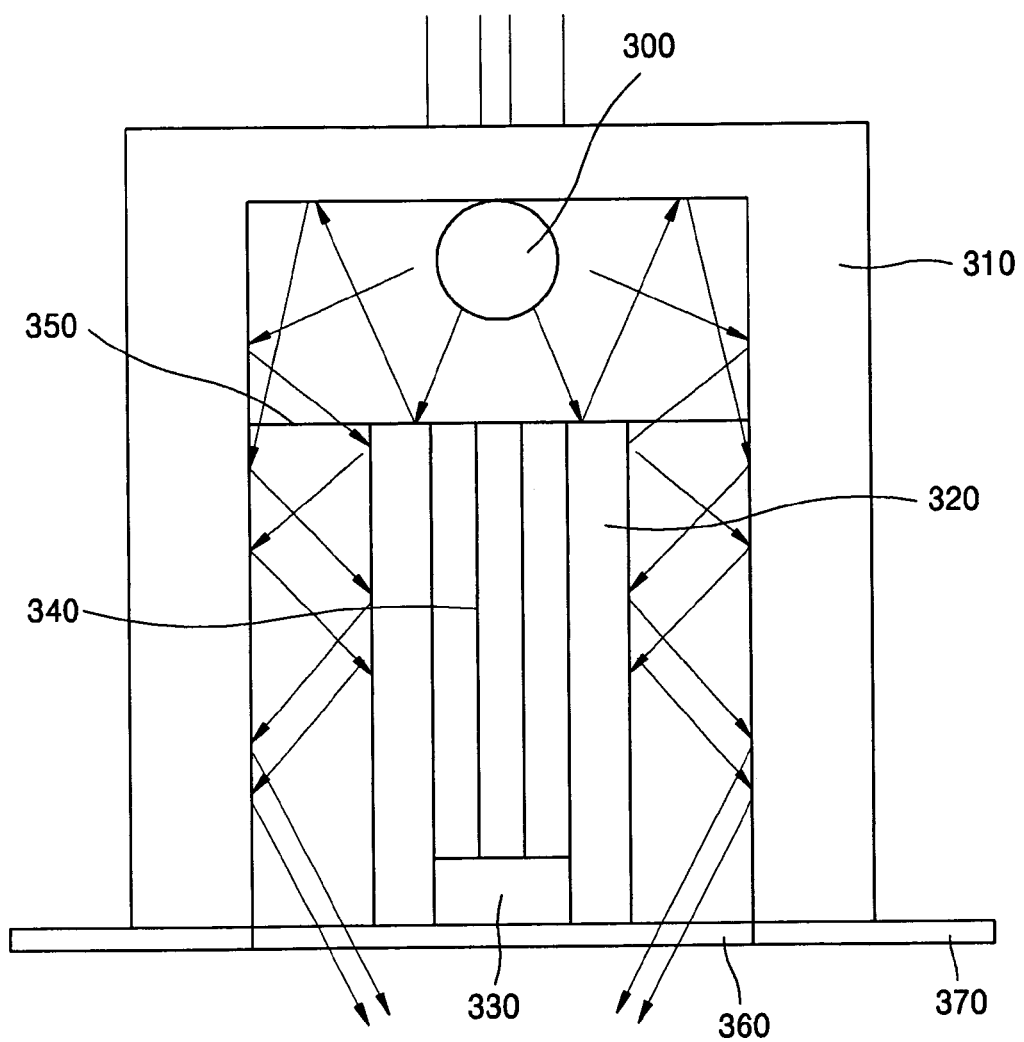
FIG. 3 illustrates a vertical cross-section of an apparatus for measuring fat thickness using near infrared rays according to an embodiment of the present invention.

FIG. 3 illustrates a vertical cross-section of an apparatus for measuring the fat thickness using near infrared rays according to an embodiment of the present invention. The apparatus includes a light emitter 300, an outer reflector 310, an inner reflector 320, a light receiver 330, signal transmitters 340 and 350, a conductive window 360, a shield 370, and a calculator (not shown).

The light emitter 300 emits near infrared rays toward a target body part. The near infrared rays emitted by the light emitter 300 may have a wavelength of 930 or 1040 nm.

The outer reflector 310 has a reflecting plane inside so that the near infrared rays emitted by the light emitter 300 are reflected from the inside reflecting plane toward the target body part. The inside of the outer reflector 310 may be formed using plastic coated with aluminum.

The inner reflector 320 has a reflecting plane outside so that the near infrared rays emitted by the light emitter 300 are reflected from the outside reflecting plane toward the target body part. The outside of the inner reflector 320 may be formed using plastic coated with aluminum.

The near infrared rays emitted by the light emitter 300 are reflected by the inside of the outer reflector 310 and the outside of the inner reflector 320 and uniformly radiated at the target body part through a space between the outer reflector 310 and the inner reflector 320.

The light receiver 330 receives the near infrared rays that are not absorbed into the target body part but are reflected therefrom. The absorptance of the target body part can be obtained by calculating a ratio of the amount of near infrared rays received by the receiver 330 to the amount of near infrared rays emitted by the light emitter 300. The light receiver 330 may be implemented as a pin type silicon detector.

The signal transmitters 340 and 350 transmit a light signal generated by the receiver 330 to the calculator. The signal transmitters 340 and 350 may be implemented as a thin metal pole whose outside is coated with aluminum.

The conductive window 360 enables the near infrared rays emitted by the light emitter 300 to reach the target body part. The shield 370 interrupts external light to prevent light other than the near infrared rays emitted by the light emitter 300 from being radiated at the target body part.

The calculator receives the light signal transmitted from the light receiver 330 through the signal transmitter 340 and 350 and calculates a fat thickness in the target body part using the light signal. For example, the calculator may calculate a ratio of the intensity of the light reflected from the target body part to the intensity of the near infrared rays radiated at the target body part and generate an equation defining the relationship between the calculated ratio and the fat thickness, thereby calculating the fat thickness in the target body part. The equation may be:

$$\text{Fat thickness} = K_0 + K_1 \times (\log 1/I)$$

$$I = E_s/E_r, \quad (1)$$

where $E_r$ is the intensity of the near infrared rays that are emitted by the light emitter 300 and radiated at the target body part, $E_s$ is the intensity of the light that is reflected from the target body part and received by the light receiver 330, and $K_0$ and $K_1$ are constants.

Figure 4:
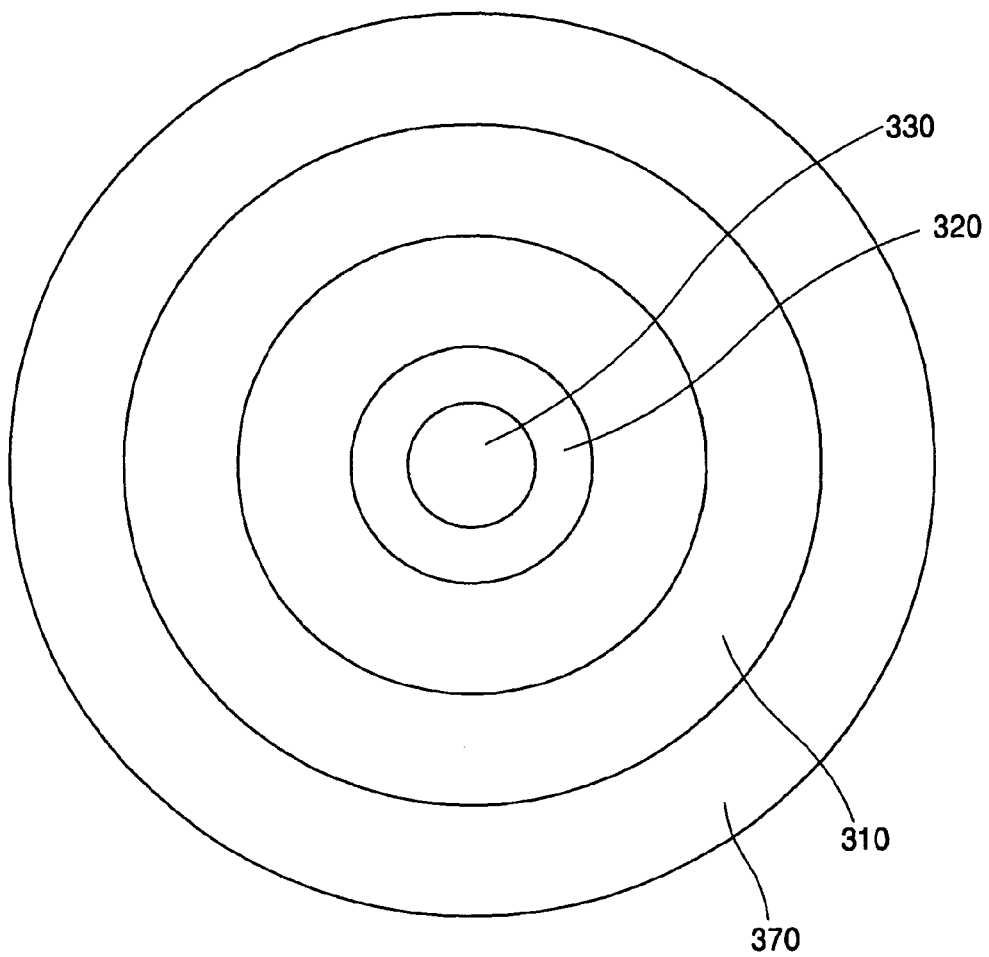
FIG. 4 illustrates a horizontal cross-section of the apparatus shown in FIG. 3.

FIG. 4 illustrates a horizontal cross-section of the apparatus shown in FIG. 3. As shown in FIG. 4, the apparatus may have a cylindrical shape. Starting from the outside of the cylindrical shape, the shield 370, the outer reflector 310, the inner reflector 320, and light receiver 330 are sequentially disposed. A passage through which the near infrared rays pass is present between the outer reflector 310 and the inner reflector 320.

Figure 5:
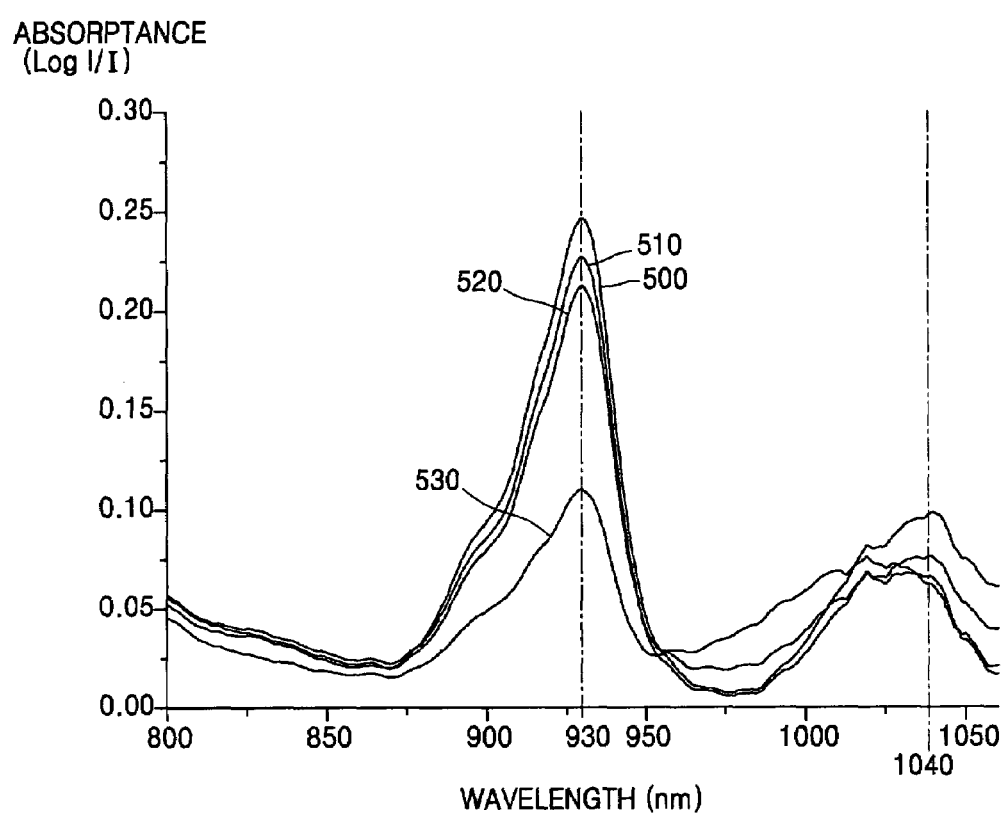
FIG. 5 is a graph illustrating the relationship between the wavelength of near infrared rays radiated at a target body part and absorptance.

FIG. 5 is a graph illustrating the relationship between the wavelength of near infrared rays radiated at a target body part and the absorptance. Curves 500, 510, 520, and 530 correspond to fat thicknesses of 10, 7, 5, and 2 mm, respectively. According to the graph shown in FIG. 5, when the near infrared rays have wavelengths of 930 and 1040 nm, absorptance of the target body part with respect to the near infrared rays increases as the fat thickness increases. Consequently, a fat thickness in the target body part can be obtained by radiating near infrared rays having a wavelength of 930 or 1040 nm at the target body part, receiving light reflected from the target body part, calculating the absorptance of the target body part, and calculating an equation like Equation (1) defining the relationship between the absorptance and the fat thickness.

Figure 6:
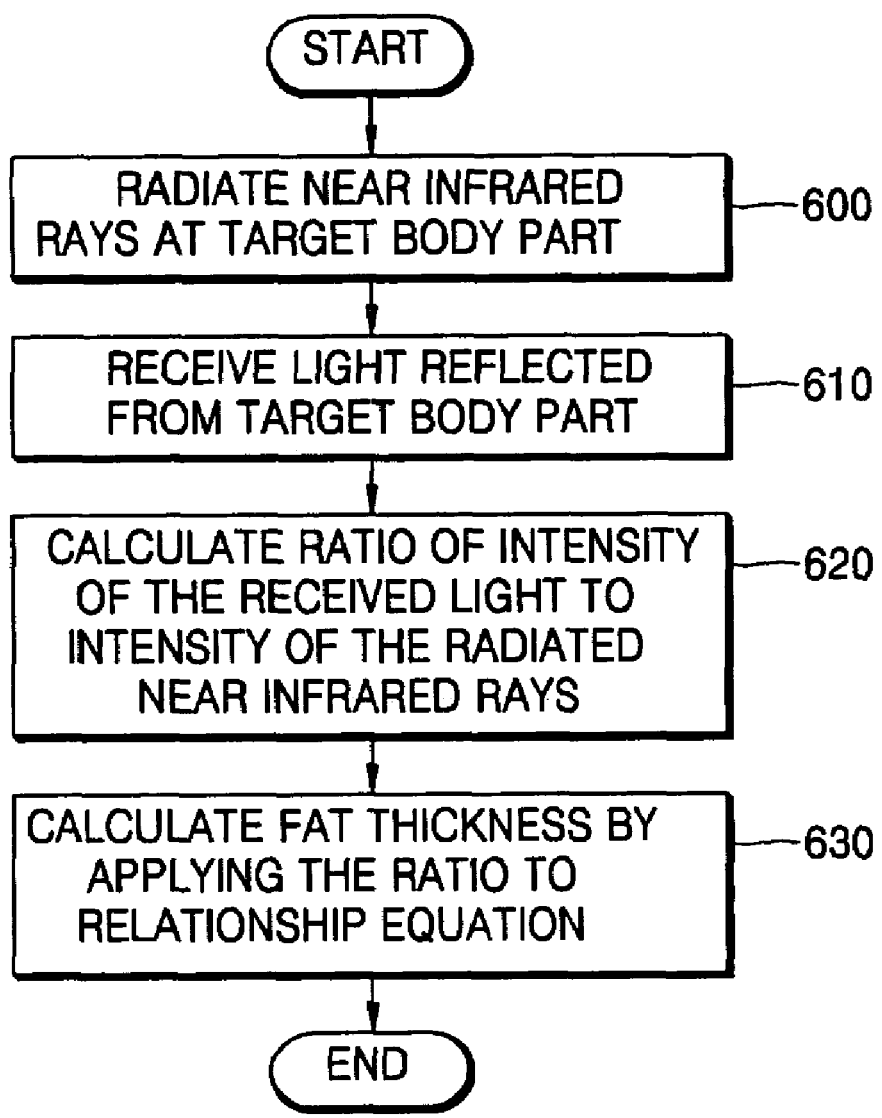
FIG. 6 is a flowchart of a method of measuring a fat thickness using near infrared rays according to an embodiment of the present invention.

FIG. 6 is a flowchart of a method of measuring fat thickness using near infrared rays according to an embodiment of the present invention. In operation 600, the light emitter 300 radiates near infrared rays at a target body part. As shown in FIG. 5, since the absorptance is proportional to the fat thickness when the near infrared rays have a wavelength of 930 or 1040 nm, it is preferable to radiate the near infrared rays having a wavelength of 930 or 1040 nm.

In operation 610, the light receiver 330 receives light reflected from the target body part at which the near infrared rays are radiated. In operation 620, the calculator calculates the intensity of the light received by the light receiver 330, and calculates absorptance, i.e., a ratio of the intensity of the light received by the light receiver 330 to the intensity of the near infrared rays radiated at the target body part. In operation 630, the calculator calculates a fat thickness in the target body part using the absorptance of the target body part.

Figure 7:
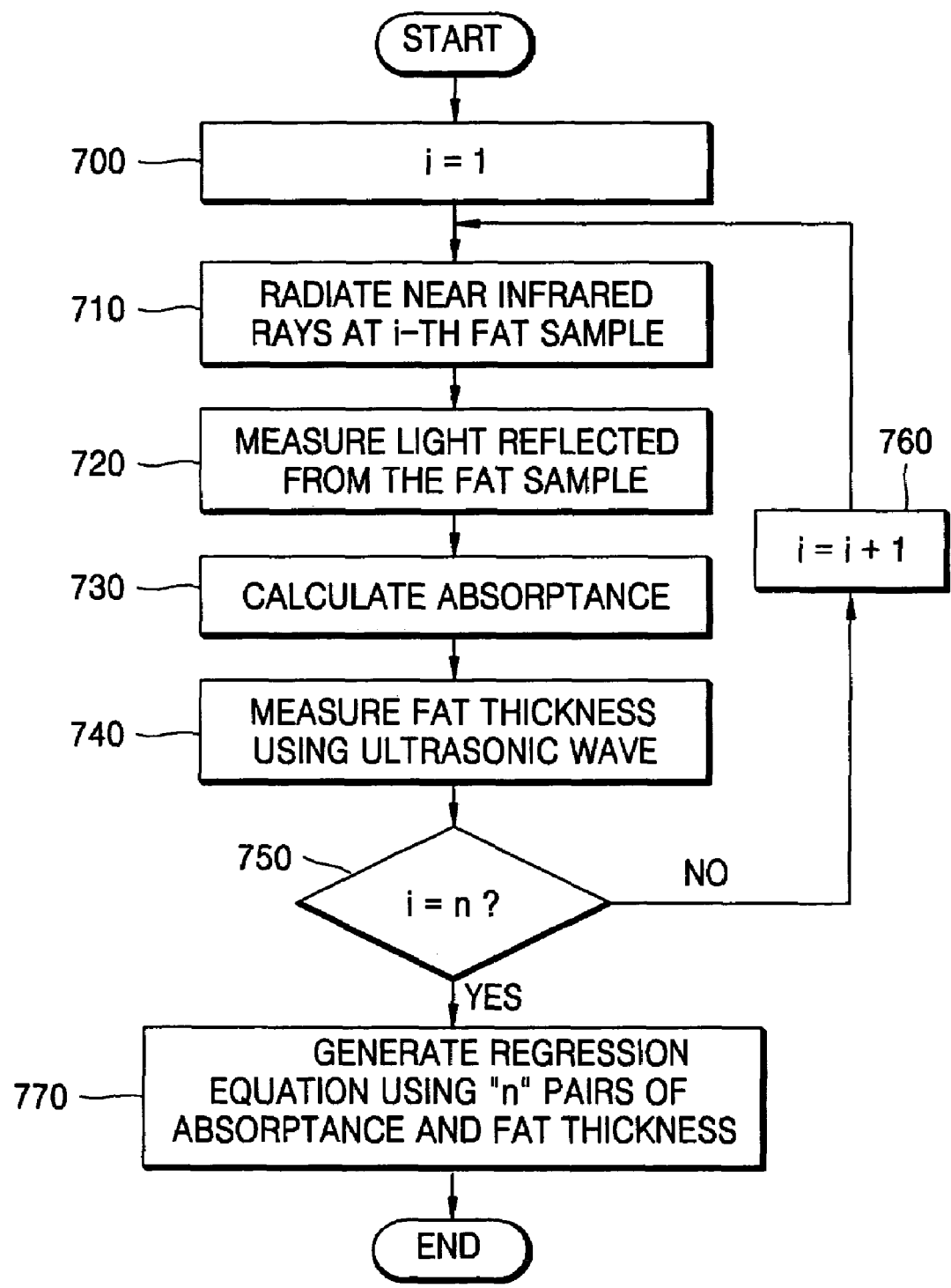
FIG. 7 is a flowchart of a method of generating a regression equation defining the relationship between the absorptance and the fat thickness.

FIG. 7 is a flowchart of a method of generating an equation defining the relationship between the absorptance and the fat thickness. In operations 700 and 710, "n" fat samples having different thicknesses are prepared and near infrared rays having a wavelength of 930 nm are radiated at a first fat sample among the "n" fat samples. In operation 720, the intensity of light reflected from the fat sample at which the near infrared rays are radiated is measured. In operation 730, absorptance of the fat sample with respect to the near infrared rays is calculated by calculating a ratio of the intensity of the light reflected from the fat sample to the intensity of the near infrared rays radiated at the fat sample.

In operation 740, the thickness of the fat sample is measured using an ultrasonic wave. In operation 750, it is determined whether the above operations are performed on all of the fat samples. Operations 710 through 740 are repeated until the absorptance and the thickness are measured with respect to all of the fat samples.

In operation 770, a regression equation defining the relationship between the absorptance and the fat thickness is generated using "n" pairs of absorptance and fat thickness measured from all of the fat samples.

To generate a more accurate equation for the relationship between the absorptance and the fat thickness, operations 700 through 760 may be repeated at two different wavelengths of the near infrared rays, and as a result, a regression equation like Equation (2) may be obtained.

$$\text{Fat thickness} = K_0 + K_1 \times (\log 1/I_1) + K_2 \times (\log 1/I_2)$$

$$I_1 = E_{s1}/E_{r1}$$

$$I_2 = E_{s2}/E_{r2} \quad (2)$$

where $E_{r1}$ is the intensity of the near infrared rays having a first wavelength that are radiated at the target body part by the light emitter 300, $E_{s1}$ is the intensity of light reflected from the target body part at which the near infrared rays having the first wavelength are radiated, $E_{r2}$ is the intensity of the near infrared rays having a second wavelength that are radiated at the target body part by the light emitter 300, $E_{s2}$ is the intensity of light reflected from the target body part at which the near infrared rays having the first wavelength are radiated, and $K_0$, $K_1$ and $K_2$ are constants. The first and second wavelengths may be 930 and 1040 nm, respectively.

When fat thickness is calculated using Equation (2), near infrared rays having the first wavelength are radiated at a target body part, and an absorptance of the target body part with respect to the near infrared rays is calculated. Thereafter, near infrared rays having the second wavelength are radiated at the target body part, and an absorptance of the target body part with respect to the near infrared rays is calculated. Next, the two absorptances are applied to Equation (2) to calculate the fat thickness in the target body part.

The invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, and carrier waves (such as data transmission through the Internet). The computer readable recording medium can also be distributed over network coupled computer systems so that the computer readable code is stored and executed in a distributed fashion. Also, functional programs, codes, and code segments for accomplishing the present invention can be easily construed by programmers skilled in the art to which the present invention pertains.

As described above, according to the present invention, near infrared rays can be uniformly radiated at a target body part using a single light emitter, and therefore, manufacturing cost and a size of a measuring apparatus can be reduced. In addition, since a fat thickness can be locally measured at a desired body part, health and obesity can be locally managed throughout the whole body.

Although a few embodiments of the present invention have been shown and described, it will be understood by those skilled in the art that changes may be made in these elements without departing from the spirit and scope of the invention, the scope of which is defined in the appended claims and their equivalents.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An apparatus for measuring fat thickness in a target body part of a person, the apparatus comprising:
   a single light emitter emitting near infrared rays;
   an inner reflector having a reflecting plane outside to reflect the near infrared rays emitted by the light emitter;
   an outer reflector surrounding the inner reflector and having a reflecting plane inside to reflect the near infrared rays emitted by the light emitter;
   a light receiver receiving light reflected from the target body part in response to the near infrared rays; and
   a calculator calculating the fat thickness in the target body part using the light received by the light receiver,
   wherein the calculator comprises:
      a ratio calculator calculating a ratio of intensity of the light received by the light receiver to intensity of the near infrared rays radiated at the target body part to obtain absorptance, and
      a thickness calculator calculating the fat thickness in the target body part using the calculated absorptance and a relationship between the absorptance and the fat thickness.

2. The apparatus of claim 1, further comprising a conductive window transmitting the near infrared rays emitted by the light emitter to the target body part.

3. The apparatus of claim 1, further comprising at least one signal transmitter transmitting the light from the light receiver to the calculator,
   wherein the signal transmitter is formed using aluminum.

4. The apparatus of claim 1, wherein the near infrared rays have a wavelength of 930 nm.

5. The apparatus of claim 1, wherein the near infrared rays have a wavelength of 1040 nm.

6. The apparatus of claim 1, wherein the reflecting planes are formed using aluminum.

7. The apparatus of claim 1, wherein the light receiver is a pin type silicon detector.

8. The apparatus of claim 1, wherein the relationship between the absorptance and the fat thickness is determined by a relationship between a ratio of intensity of light reflected from a fat to intensity of near infrared rays radiated at the fat and a thickness of the fat measured using an ultrasonic wave.

9. The apparatus of claim 1, wherein the calculator comprises:
   a ratio calculator calculating a ratio of intensity of the light received by the light receiver to intensity of the near infrared rays radiated at the target body part to obtain absorptance; and
   a thickness calculator calculating the fat thickness in the target body part using two absorptances calculated with respect to the near infrared rays having two different wavelengths and a relationship between the absorptances and the fat thickness.

10. A method of measuring fat thickness in a target body part of a person, the method comprising:
    radiating near infrared rays at a fat sample, measuring an absorptance of the fat sample with respect to the near infrared rays, measuring a thickness of the fat sample using an ultrasonic wave, and generating an equation defining a relationship between the absorptance and the fat thickness;
    generating and radiating near infrared rays at the target body part;
    receiving light reflected from the target body part in response to the near infrared rays;
    calculating a ratio of intensity of the light reflected from the target body part to intensity of the near infrared rays radiated at the target body part to obtain absorptance of the target body part; and
    calculating the fat thickness in the target body part using the calculated absorptance and the generated equation,
    wherein the near infrared rays are emitted by a single light emitter.

11. The method of claim 10, wherein the light is received by a pin type silicon detector.

12. The method of claim 10, wherein the near infrared rays have a wavelength of 930 nm.

13. The method of claim 10, wherein the near infrared rays have a wavelength of 1040 nm.

14. A method of measuring fat thickness in a target body part of a person, the method comprising:
    radiating near infrared rays having a first wavelength at a fat sample and measuring an absorptance of the fat sample with respect to the near infrared rays having the first wavelength;
    radiating near infrared rays having a second wavelength at the fat sample and measuring an absorptance of the fat sample with respect to the near infrared rays having the second wavelength;
    measuring a thickness of the fat using an ultrasonic wave;
    generating an equation defining a relationship between the absorptances respectively obtained at the first and second wavelengths and the fat thickness;
    radiating near infrared rays having the first wavelength at the target body part, receiving light reflected from the target body part, and calculating a ratio of intensity of the light reflected from the body part to intensity of the near infrared rays radiated at the target body part to obtain absorptance of the target body part;
    radiating near infrared rays having the second wavelength at the target body part, receiving light reflected from the target body part, and calculating a ratio of intensity of the light reflected from the body part to intensity of the near infrared rays radiated at the target body part to obtain absorptance of the target body part; and
    calculating the fat thickness in the target body part using the two calculated absorptances and the generated equation,
    wherein the near infrared rays are emitted by a single light emitter.

15. The method of claim 14, wherein the first and second wavelengths are 930 nm and 1040 nm, respectively.

16. A computer readable recording medium including processing instructions providing a method executable by an apparatus measuring fat thickness in a target body part of a person, the method comprising:
    radiating near infrared rays at a fat sample, measuring an absorptance of the fat sample with respect to the near infrared rays, measuring a thickness of the fat sample using an ultrasonic wave, and generating an equation defining a relationship between the absorptance and the fat thickness;
    generating and radiating near infrared rays at the target body part;
    receiving light reflected from the target body part in response to the near infrared rays;
    calculating a ratio of intensity of the light reflected from the target body part to intensity of the near infrared rays radiated at the target body part to obtain absorptance of the target body part; and calculating the fat thickness in the target body part using the calculated absorptance and the generated equation, wherein the near infrared rays are emitted by a single light emitter.

17. A computer readable recording medium including processing instructions providing a method executable by an apparatus measuring fat thickness in a target body part of a person, the method comprising:

radiating near infrared rays having a first wavelength at a fat sample and measuring an absorptance of the fat sample with respect to the near infrared rays having the first wavelength;

radiating near infrared rays having a second wavelength at the fat sample and measuring an absorptance of the fat sample with respect to the near infrared rays having the second wavelength;

measuring a thickness of the fat using an ultrasonic wave;

generating an equation defining a relationship between the absorptances respectively obtained at the first and second wavelengths and the fat thickness;

radiating near infrared rays having the first wavelength at the target body part, receiving light reflected from the target body part, and calculating a ratio of intensity of the light reflected from the body part to intensity of the near infrared rays radiated at the target body part to obtain absorptance of the target body part;

radiating near infrared rays having the second wavelength at the target body part, receiving light reflected from the target body part, and calculating a ratio of intensity of the light reflected from the body part to intensity of the near infrared rays radiated at the target body part to obtain absorptance of the target body part; and calculating the fat thickness in the target body part using the two calculated absorptances and the generated equation, wherein the near infrared rays are emitted by a single light emitter.

* * * * *

UNITED STATES PATENT AND TRADEMARK OFFICE
CERTIFICATE OF CORRECTION

PATENT NO. : 7,574,252 B2 Page 1 of 1
APPLICATION NO. : 11/192117
DATED : August 11, 2009
INVENTOR(S) : Jong-youn Lee et al.

It is certified that error appears in the above-identified patent and that said Letters Patent is hereby corrected as shown below:

Column 8, Line 52, after "apparatus" insert --for--.

Column 9, Line 7, after "apparatus" insert --for--.

Signed and Sealed this

Seventeenth Day of November, 2009

David J. Kappos
*Director of the United States Patent and Trademark Office*